United States Patent
Ginn et al.

[19]

[11] Patent Number: 5,871,496
[45] Date of Patent: Feb. 16, 1999

[54] SURGICAL INSTRUMENT FOR FACILITATING THE DETACHMENT OF AN ARTERY AND THE LIKE

[75] Inventors: Richard S. Ginn, San Jose, Calif.; Hani Shennib, Quebec, Canada; Charles S. Taylor, San Francisco; Ivan Sepetka, Los Altos, both of Calif.

[73] Assignee: Cardiothoracic Systems, Inc., Cupertino, Calif.

[21] Appl. No.: 835,675

[22] Filed: Apr. 10, 1997

Related U.S. Application Data

[63] Continuation-in-part of Ser. No. 619,046, Mar. 20, 1996, abandoned.

[51] Int. Cl.⁶ .................................................. A61B 17/00
[52] U.S. Cl. ........................................ 606/190; 606/159
[58] Field of Search .................... 606/190, 159, 606/205–208, 185, 147, 148

[56] References Cited

U.S. PATENT DOCUMENTS

| | | |
|---|---|---|
| 4,671,274 | 6/1987 | Sorochenko . |
| 5,013,312 | 5/1991 | Parins et al. . |
| 5,199,419 | 4/1993 | Remiszewski et al. . |
| 5,381,788 | 1/1995 | Matula et al. . |
| 5,569,204 | 10/1996 | Cramer ...................................... 606/159 |
| 5,569,270 | 10/1996 | Weng . |
| 5,591,183 | 1/1997 | Chin . |
| 5,601,581 | 2/1997 | Fogarty et al. . |
| 5,667,480 | 9/1997 | Knight et al. ............................ 606/159 |

FOREIGN PATENT DOCUMENTS

WO93/13713  7/1993  European Pat. Off. .

OTHER PUBLICATIONS

Surgical Innovations Limited EndoFlex Endoscopic Retraction System Product Insert (2 pages).

*Primary Examiner*—Michael Buiz
*Assistant Examiner*—Kevin Truong
*Attorney, Agent, or Firm*—Lyon & Lyon LLP

[57] ABSTRACT

A surgical instrument is configured to aid in performing a procedure of detaching an internal mammary artery (IMA) and the like, from the connecting tissues and side branch vessels which surround the artery in its native location, wherein the detaching procedure is preliminary to the performing of a coronary artery bypass grafting procedure and wherein the IMA is detached via a minimally invasive thoracotomy. To this end, an elongated slender rod includes a handle at its proximal end and an artery engaging loop, arc, fork configuration, or hook at its distal working end. Embodiments may incorporate electrosurgical capability or electrical insulation. A surgeon thus has means for harvesting an intact and undamaged graft vessel from its native location through a minimally invasive incision with enhanced speed, visibility, and freedom of motion.

11 Claims, 8 Drawing Sheets

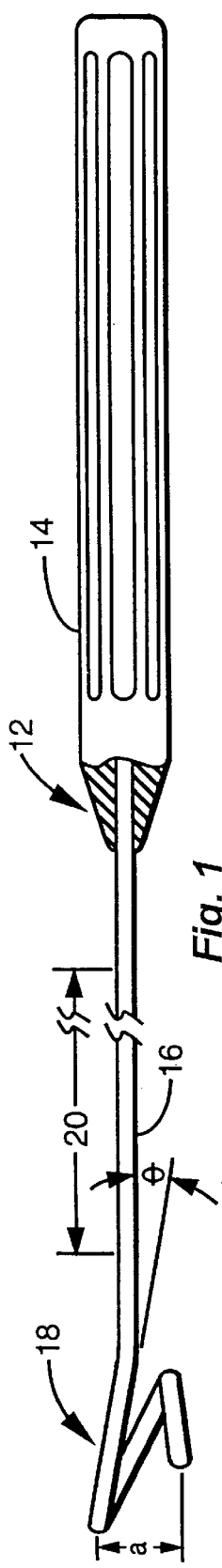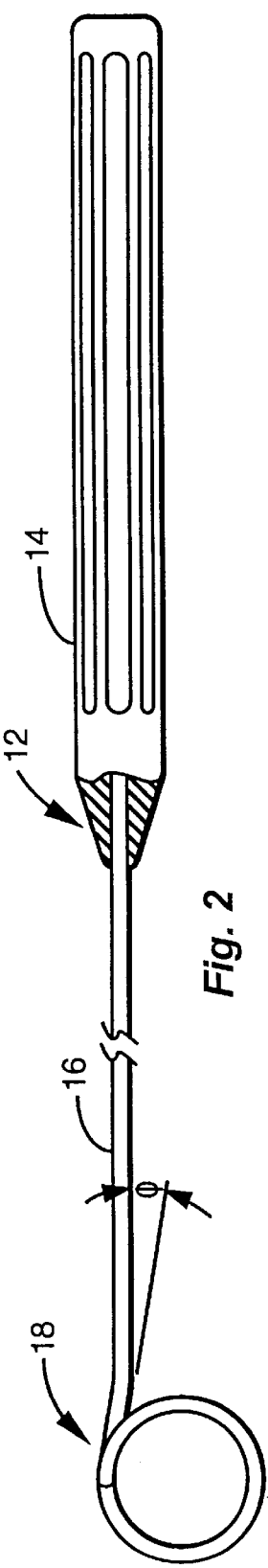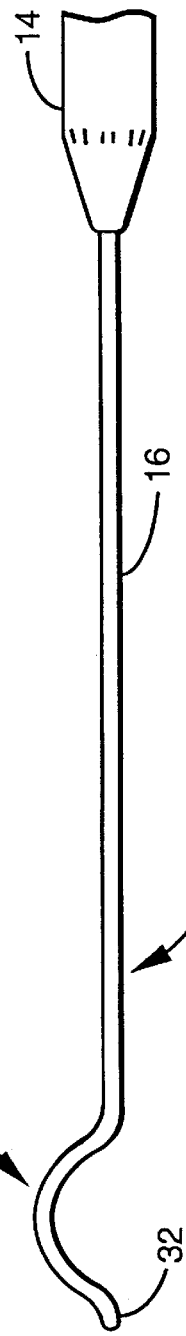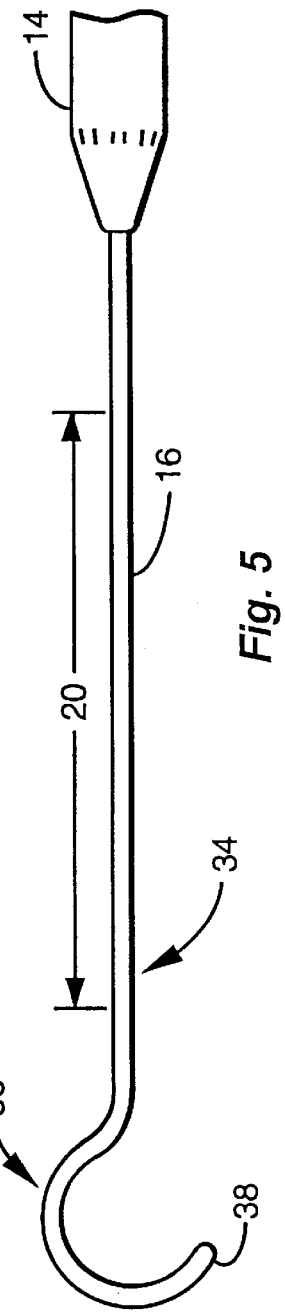
Fig. 1
Fig. 2
Fig. 4
Fig. 5

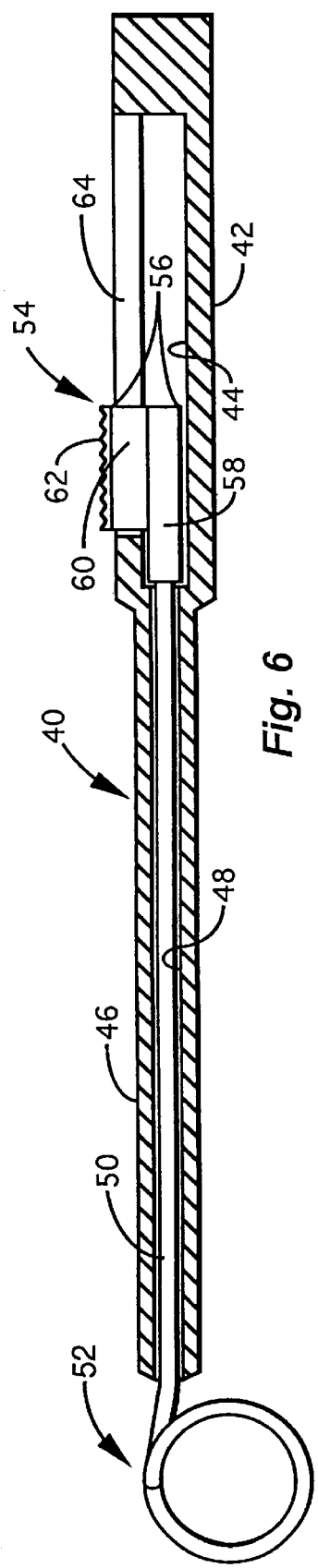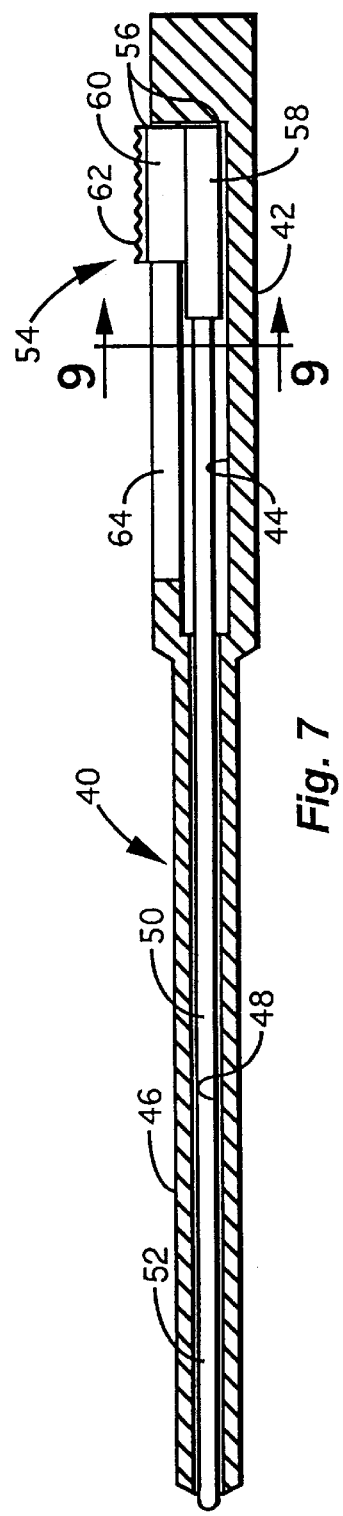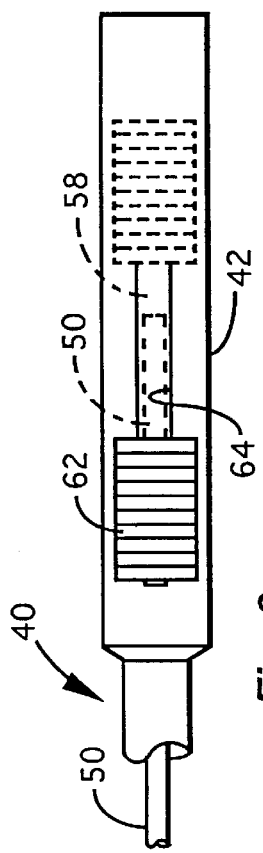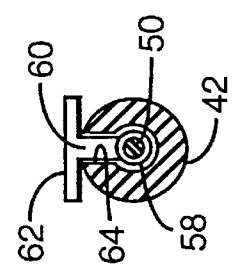

SURGICAL INSTRUMENT FOR FACILITATING THE DETACHMENT OF AN ARTERY AND THE LIKE

This application is a continuation-in-part of application Ser. No. 08/619,046, filed on Mar. 20, 1996 now abandoned, the disclosures of which are incorporated herein by reference as if set forth in full.

FIELD OF THE INVENTION

The present invention relates to minimally invasive surgical instruments and procedures and, in particular, to surgical tools for dissecting and manipulating an artery, such as the internal mammary artery (IMA), from its natural location in connection with a coronary artery bypass grafting (CABG) procedure.

BACKGROUND OF THE INVENTION

Surgeons are constantly striving to develop advanced surgical techniques resulting in the need for advanced surgical devices and instruments required to perform such techniques. Recent advances in the surgical field are increasingly related to surgical procedures which are less invasive and reduce the overall trauma to the patient. To illustrate, in a conventional CABG procedure it has been common practice for surgeons to perform a sternotomy to expose the body cavity in the thoracic region. To this end, a surgeon makes a long incision down the middle of a patient's chest, saws through the length of the sternum and spreads the two halves of the sternum apart. Retractors then are employed to provide access to the vessels where an anastomosis will be performed. The CABG procedure is further complicated by the need to stop the beating of the heart by means of cardioplegia and to attach the patient to a cardiopulmonary bypass (CPB) machine to continue the circulation of oxygenated blood to the rest of the body while the graft is sewn in place.

In a procedure known as an "in situ bypass graft," the surgeon dissects a sufficient length of the artery from its connective tissue, then transects the artery, and connects the transected end to a diseased target coronary artery distal to an obstruction, while leaving the other end of the dissected artery attached to the arterial supply, thus restoring blood perfusion to the heart.

The internal mammary arteries (IMAs), left (LIMA) and right (RIMA), are particularly desirable for use as in situ bypass grafts as they are conveniently located, have diameters and blood flow volumes that are comparable to those of coronary arteries, and in practice typically have superior patency rates. Extending from the subclavian arteries near the neck to the diaphragm and running along the backside of the ribs adjacent the sternum, the IMAs deliver blood to the musculature of the chest wall. The LIMA is typically used as an arterial source for target locations on the left anterior descending coronary artery (LAD), the diagonal coronary artery (Dx), the circumflex artery (Cx), the obtuse marginal artery, and the ramus intermedius coronary artery. The RIMA is typically used for connection to all of the same target locations, as well as the right coronary artery (RCA) and the posterior descending artery.

Use of either IMA as a bypass graft first involves harvesting the IMA free from the inside chest wall. In conventional CABG approaches, access to the IMA is obtained through a sternotomy or major thoracotomy incision (involving sawing through one or more ribs) through the chest. Harvesting of the IMAs is accomplished with relative ease due to the working space made available by the sternotomy or major thoracotomy.

An IMA is detached from its connective tissue until there is sufficient slack in the IMA to allow the distal end thereof to be attached to an incision, generally in the left anterior descending coronary artery (LAD). In preparation for the in situ bypass graft, the sternotomy procedure provides the surgeon with ready access to the IMA since it is exposed by the spreading of the sternum. The IMA thus may be transected at its distal end and detached from the connective tissues in its native location in the sternum region, while still attached at its proximal end to its arterial supply, using the usual surgical instruments such as scalpels, scissors, forceps, etc.

The CABG procedure would be improved if surgeons could avoid the need for arresting the heart, thereby eliminating the need to connect the patient to a cardiopulmonary bypass machine to sustain the patient's life. To this end, recent developments lend themselves to CABG procedures using surgical techniques which enable surgeons to perform the procedure while the heart is beating. This eliminates the need for the lengthy and traumatic cardiopulmonary bypass procedure, cardioplegia is unnecessary, the overall surgery is much less invasive and traumatic, and patient recovery time and costs are reduced.

Recently, progress has been made in advancing minimally invasive surgical techniques, particularly in cardiothoracic surgery, which eliminates the need for a sternotomy or major thoracotomy. Access to the heart with these minimally invasive techniques is obtained through one very small surgical incision (minimal thoracotomy) or through several percutaneous cannulas known as trocar sleeves positioned intercostally in the thoracic cavity of the patient. Visualization of the operative area may be facilitated by thoracoscopes which typically consist of a video camera configured for introduction through a small incision or trocar sleeve to allow observation of the target area on a video monitor.

With the advent of these minimally invasive techniques, harvesting the IMA has become more complex and difficult due to a restricted work space and access, and to reduced visualization of the IMA. The in situ bypass graft procedure and thus the procedure of detaching the IMA likewise must be performed through the minimal thoracotomy. Surgeons presently perform the procedure of detaching the IMA from its native location with the aid of the usual instruments such as the scalpels, scissors and forceps of previous mention. These instruments are not specially designed for use in less invasive procedures and do not facilitate the desired gentle handling of the IMA as it is detached from the surrounding connective tissues to provide the bypass graft for the CABG procedure. The harvesting procedure itself may actually be lengthened and the trauma to the vessel potentially increased by the less invasive techniques, in part because a number of tools must be introduced and exchanged through the restricted incision(s). This is a concern as a high degree of precision is required when harvesting a bypass vessel to avoid injury (such as over cutting or cauterizing) to the vessel which may in turn lead to increased rates of occlusion in the vessel in the months and years after the procedure.

Although low-profile micro-surgical instruments are readily available for some procedures, such has not been the case for harvesting the IMA and other similarly situated arteries in minimally invasive CABG procedures. Surgical instruments designed for laparoscopic and other minimally invasive applications are not generally suitable for performing minimally invasive CABG. Most laparoscopic procedures, for example, target body structures which are quite large in comparison to coronary vessels, and do not require the high degree of precision required in a CABG procedure. Accordingly, laparoscopic instruments generally provide only limited angular orientation, making them unsuitable for harvesting of the IMA and other similarly situated arteries through a minimal thoracotomy or an intercostal puncture site.

Typically an electrosurgical tool (often called a "Bovie") similar to that described in U.S. Pat. No. 5,013,312 is used to free a length of the IMA by incising the endothoracic fascia and severing the side branch vessels to free the IMA. The use of such electrosurgical devices is well known in the art and can be crucial in controlling bleeding during harvesting of the IMA. Such devices are typically in the form of scalpels, forceps, and scissors, and employ at least one conductive electrode connected thereto.

Despite the use of an electrosurgical tool, because initial cauterization may be applied over too short a length of a vessel or side branch to be complete, it is common practice to apply sutures or surgical clips to control bleeding before complete coagulation is effected. Applying and removal of clips or sutures can be time-consuming. In addition, if clips are accidentally loosened and dropped inside the patient's body cavity, there can be serious complications and additional expenditure of time in the procedure.

When an electrosurgical tool is used in simultaneous conjunction with other instruments that are not electrically insulated, there is a serious risk of accidental electric short-circuiting or arcing due to contact or close proximity. This can lead to traumatic electric shock to the patient or the surgeon, damage to an instrument, disruption of the procedure, or over or under cutting or cauterization, which can adversely affect the control of bleeding or the integrity and patency of the graft vessel.

A bipolar electrosurgical instrument comprising a fork-shaped configuration is described in U.S. Pat. No. 4,671,274. This instrument combines the functions of tissue manipulation and electrocautery, and finds application for control of bleeding during the transection of blood vessels; however, it involves separate hinged jaws and cannot provide an adequate range of angular motion through a minimally invasive thoracotomy.

Accordingly, it would be highly desirable when performing a detachment, or "take-down" procedure on the IMA, to provide a specialized instrument which allows the surgeon a greater range of visibility and angular motion to harvest an intact and undamaged length of vessel more rapidly and gently with fewer instruments obstructing the operating field and with minimal risk of accidental electric shock, while the tissues and side branch vessels are being dissected with the aid of a surgical knife or scissors. It would further be desirable to reduce or eliminate the need for surgical clips or sutures in the IMA harvest procedure.

SUMMARY OF THE INVENTION

The present invention provides a specialized surgical instrument which overcomes the deficiencies of previous mention, that is, provides gentle handling of the IMA when performing the procedure of detaching the IMA from its native location during the less invasive CABG procedure using the comparatively small incision or thoracotomy in the chest. It potentially reduces the number of instruments obstructing the field and provides malleable instrument shafts, thereby allowing the surgeon a greater range of visibility and angular motion to harvest an intact and undamaged length of vessel more rapidly. It provides electrically insulated instruments and self-contained electrosurgical instruments that reduce the risk of accidental electric shock. It provides embodiments that potentially reduce the need for surgical clips or sutures to control bleeding. These advantages are also applicable to the dissection or harvesting of other vessels for use as a graft in a vascular surgical procedure.

More particularly, in selected embodiments the invention comprises an elongated slender rod, permanently attached to a handle of greater cross section configured for comfortable grasping by a surgeon. The slender rod may be formed of a material such as a firm plastic, but preferably is formed of stainless steel. The distal end of the rod is formed into a loop or coil, an arcuate segment or other preselected curved configuration which provides means for capturing the IMA, or other vessel, which is being detached, dissected or otherwise handled. The various embodiments contemplated by the invention include a full 360 degree loop configuration with the overlapped coil of the loop axially spaced apart, as well as partial loop and arcuate configurations. The distal, or working, end of the invention thus is configured and is of selected dimensions to allow a surgeon to capture a vessel at a distant location through small openings in a patient's body, and to then gently manipulate the vessel as necessary in the specific surgical procedure. Thus, the invention provides the advantage of remotely handling of a vessel with a minimum of trauma during minimally invasive surgical procedures.

In alternative embodiments, the invention includes an elongated tube coaxially attached to the handle, and a rod actuating means integral with the handle. In response to the rod actuating means, the rod and the integral working end is extended from the distal end of the tube as when in use, or may be retracted into the tube when not in use.

In further alternative embodiments, the invention includes a fork configuration that can engage and manipulate a vessel and connective tissue. These embodiments facilitate safe and rapid severing of the many side branches that must be separated from the main vessel, with minimal bleeding or damage to the harvested vessel. Described configurations protect the harvested vessel from accidental damage by an electrosurgical knife. Instruments according to the invention are coated with electrically insulating material to prevent accidental short-circuiting and arcing when used with electrosurgical tools. Other embodiments incorporate self-contained unipolar or bipolar electrosurgical capabilities, thereby eliminating the need for extra instruments, potentially reducing or eliminating the need for surgical clips or sutures to control bleeding, and improving the accuracy, speed, and safety of vascular graft dissection.

BRIEF DESCRIPTION OF THE DRAWINGS

FIGS. 1 and 2 are top and elevational views, respectively, of an embodiment of the present invention.

FIGS. 4 and 5 are elevational views of alternative embodiments of the invention.

FIGS. 6 and 7 are elevational views of a further alternative embodiment of the invention embodying a retractable distal working end.

FIG. 8 is a partial top view of the embodiment of FIGS. 6, 7.

FIG. 9 is a cross-sectional view taken along section line 9—9 of FIG. 7.

DETAILED DESCRIPTION OF THE EMBODIMENTS

Figure 3:
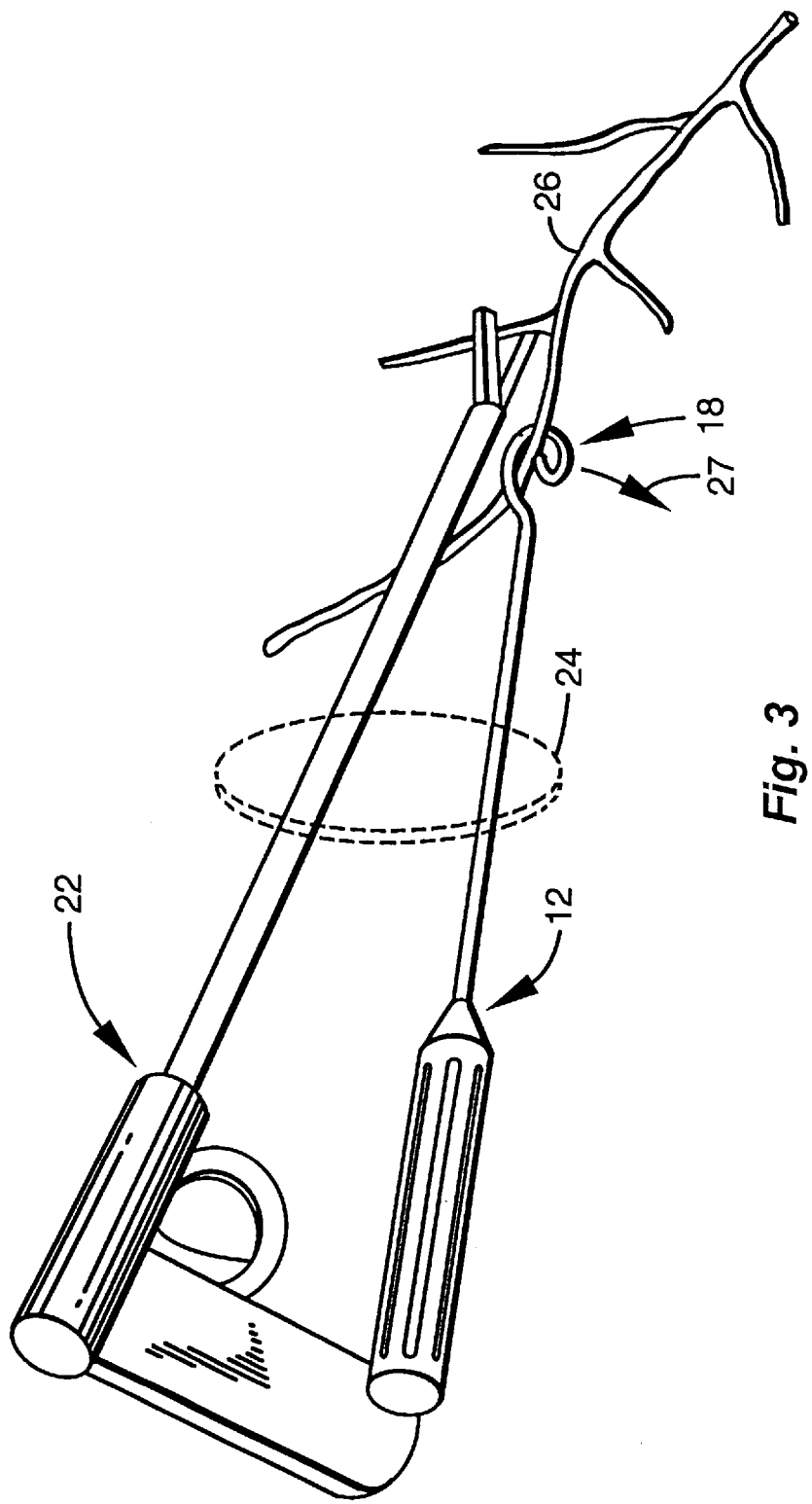
FIG. 3 is a perspective view illustrating a use of the invention in cooperation with surgical scissors when performing the procedure of detaching the IMA from its native location.

FIGS. 1 and 2 illustrate one embodiment 12 of a surgical instrument in accordance with the present invention, which includes a handle 14 at the proximal end securely attached to, or formed as part of, an elongated slender rod 16. Rod 16 may have a circular, oval, rectangular, triangular or other cross-sectional shape over all or any portion of its length, and may be solid or hollow in whole or in part, containing one or a plurality of internal cavities. The distal end of the instrument, and particularly of rod 16, is formed into a loop 18. The loop 18 may be continued to form a complete circle as depicted in FIGS. 1 and 2, or may be of less than a full circle, such as exemplified by the arcuate embodiments depicted in FIGS. 4 and 5 below. Loop 18 has an inside diameter of the order of one-half to three-quarter inch, and the overlapping tip 19 of the loop is spaced from the body of the loop a distance, a, of the order of one-fourth to one-third inch. Preferably, the circumference of loop 18 does not lie in a single plane but is displaced helically to provide axial displacement between separate points on the loop. As depicted in the figures by way of example only, loop 18 is bent at an angle relative to rod 16 of approximately 10 degrees in the top view (FIG. 1), and at an angle of approximately 20 degrees in the elevational view (FIG. 2). Rod 16 and handle 14 may be formed in whole or in part of stainless steel, aluminum, or plastic, respectively. If a combination of materials is used, the rod is bonded or glued to the handle via a suitable axial bore in the handle. It may be preferable for use in electrosurgical procedures that the instrument be non-conductive electrically; accordingly, if rod 16 (and/or handle 14) is formed of stainless steel or other electrically conductive material, it may be coated with a non-conductive biocompatible material such as PTFE or polyamide polymer. Rod 16 and handle 14 also may be made of any of the other conventional biocompatible medical plastics having sufficient tensile and bending strength.

In a preferred embodiment, rod 16 is formed of a stainless steel material and thus is relatively resistant to force applied transversely to the rod length. However, a partial length 20 (FIG. 1) of rod 16 may be annealed to have a malleable property, whereby rod 16 can be deformed by the surgeon to tailor the precise curvature thereof depending on the nature of the procedure, the patient's anatomy, and the preferences of the surgeon. Loop 18 can likewise be annealed in whole or in part to have a malleable property.

FIG. 3 illustrates a manner of use of the invention employing the embodiment 12 of FIGS. 1 and 2. It is to be understood that any of the embodiments presented herein also may be used in similar fashion to perform the same function. To this end, surgical scissors 22 may be introduced by a surgeon through a thoracotomy 24 and used to initiate the severing of tissues from a vessel such as an IMA 26 to thus initiate detachment of a first segment of the IMA. In the following description, the IMA is used as the example, with the understanding that other vessels may be harvested using the devices and procedures of the invention. Upon slight detachment of the IMA, instrument 12 of the invention also is inserted through the thoracotomy 24 and the tip 19 of loop 18 is introduced past IMA 26. A slight twist of instrument 12 causes loop 18 to encircle the IMA whereupon the surgeon has complete control of the direction in which force may be applied to urge the IMA gently from its native location. Scissors 22 simultaneously are used to dissect tissues and side branch vessels 25 from the IMA. The surgeon may continue the procedure of dissecting the connecting tissues and side branch vessels while pulling the IMA away from the endothoracic fascia with instrument 12 as depicted by arrow 27, until a sufficient length of the IMA has been detached from the endothoracic fascia to allow performing a CABG procedure. The invention thus allows capturing the IMA and provides the surgeon thereafter with complete control of the artery to allow it to be manipulated gently in any direction during the detaching process.

FIG. 4 illustrates an alternative embodiment 28 of the invention, wherein the full loop 18 of the FIGS. 1 and 2 is defined by one or more arcuate segments, which comprise at least one arc 30 formed in the distal end of rod 16. Arc 30 terminates in a tip 32 which is bent away from the arc configuration to extend generally coaxially with rod 16. Tip 32 guides the introduction of arc 30 through the surrounding tissues and past the IMA, whereby arc 30 is used to manipulate the IMA while detaching it from the endothoracic fascia.

FIG. 5 illustrates a further alternative embodiment 34 of the invention, wherein the loop 18 of FIGS. 1 and 2 is defined by a slightly ovaled partial loop 36 of approximately three-fourths of a full oval or circle. This configuration provides a tip 38 which allows manipulating the IMA in various directions without completely encircling the artery as with loop 18. As depicted in FIG. 5, rod 16 may be annealed along a length 20 as described in FIG. 1, to allow readily deforming the rod to tailor the contour of the instrument to meet the requirements of the procedure, the anatomy of the patient, and the preferences of the surgeon to facilitate the capture and manipulation of the IMA by loop 18, arc 30 or partial loop 36.

FIGS. 6–9 depict portions of alternative embodiments 40 of the invention employing a retractable distal working end of the instrument. Rod 16 and loop 18 (or arc 30 or partial loop 36) may be retracted into a protective housing when not in use, and extended to provide loop 18 when the instrument is to be used. Instrument 40 includes a hollow handle 42 having thus a lumen 44. An elongated tube 46 is coaxially formed with the handle 42 and includes a lumen 48 extending the length of the tube 46 in communication with lumen 44. A slender elongated rod 50 similar to rod 16 of FIGS. 1, 2, 4, and 5 is dimensioned to fit in slidable relation within lumen 48 of tube 46. Rod 50 is formed, for example, of a nickel-titanium alloy material having an inherent shape-memory property. In this embodiment the distal working end of rod 50 is formed into a loop 52 similar to the loop 18 of FIGS. 1 and 2, which thus is the shape to which the shape-memory material, that is, the distal working end of rod 50, will return. It is to be understood that the distal working end of rod 50 could be formed into the arcuate or partial loop configurations of FIGS. 4 or 5, respectively, rather than the full loop configuration 18, 52. FIG. 6 depicts instrument 40 with rod 50 extended to provide an exposed vessel capturing distal working end for use by a surgeon.

FIG. 7 depicts the instrument 40 with rod 50 retracted into tube 46. As may be seen, the shape-memory material is sufficiently flexible that, when rod 50 is drawn into lumen 48 of tube 46, loop 52 is forcibly deformed to assume the shape of the lumen, that is, loop 52 is straightened. Thus, the working end of the instrument may be fully retracted into the protective housing of tube 46. When the instrument is to be used in a procedure of detaching a vessel such as the IMA from its connecting tissues, rod 50 is extended from tube 46, whereupon due to the inherent shape-memory property of the nickel-titanium alloy material, loop 52 will automatically re-form into its memorized shape depicted in FIG. 6.

Various mechanical devices may be employed with handle 42 to provide rod 50 with working end 18, 30, 36 operated by an actuating means 54. By way of example only, actuating means 54 herein includes a reciprocatable slide 56 formed with a cylindrical member 58 slidably fitted within lumen 44 of handle 42. Cylindrical member 58 is integrally formed with a radially-extending flat yoke 60 which, in turn, has a thumb-engaging member 62 secured thereto. Flat yoke 60 reciprocates within a slot 64 formed in the side wall of handle 42 in communication with lumen 44, and thumb-engaging member 62 is positioned exterior of slot 64 and outer cylindrical surface of handle 42 for access by the surgeon's thumb or fingers. Rod 50 is coaxially secured to cylindrical member 58 and thus any reciprocation of thumb-engaging member 62 imparts similar reciprocation to rod 50.

Although slidable actuating means 54 is illustrated herein, other mechanisms may be used. For example, the proximal end of rod 50 may be provided with external helical threads, wherein a coaxial circular dial with internal matching helical threads is disposed within the distal portion of handle 42 with the internal threads engaging the external threads. Selective rotation of the dial thus reciprocally translates rod 50 to extend or retract the rod and working end of instrument 40.

Figure 10:
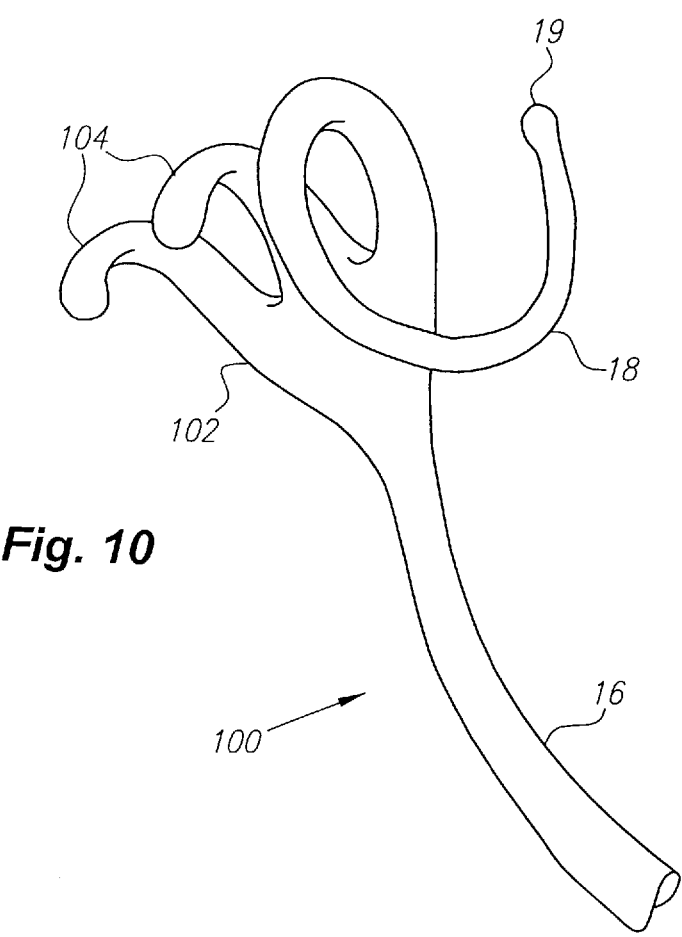
FIG. 10 shows an embodiment combining a loop with a fork configuration.
Figure 11:
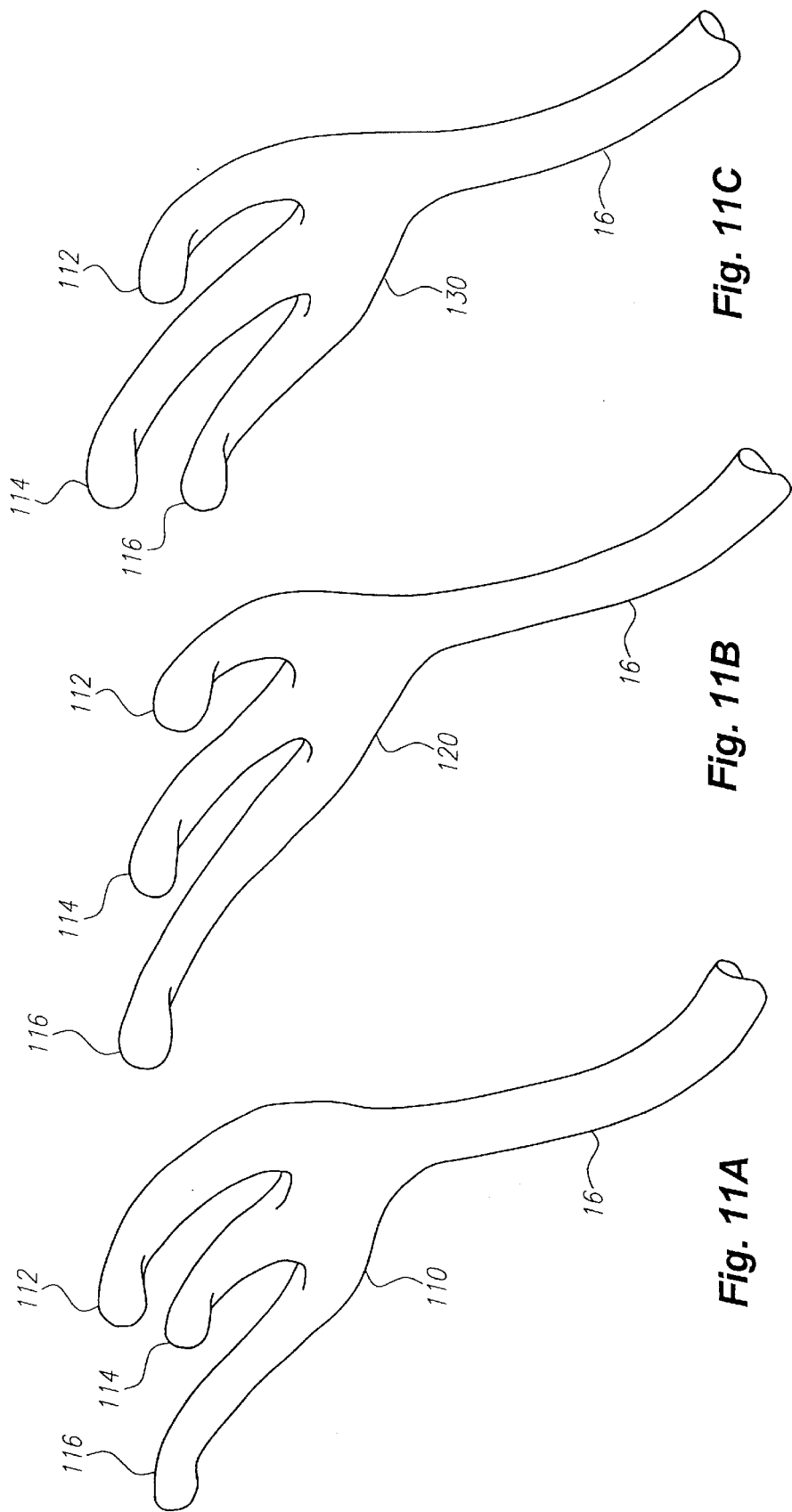
FIGS. 11A–11C illustrate fork configurations having fingers of unequal lengths.
Figure 12:
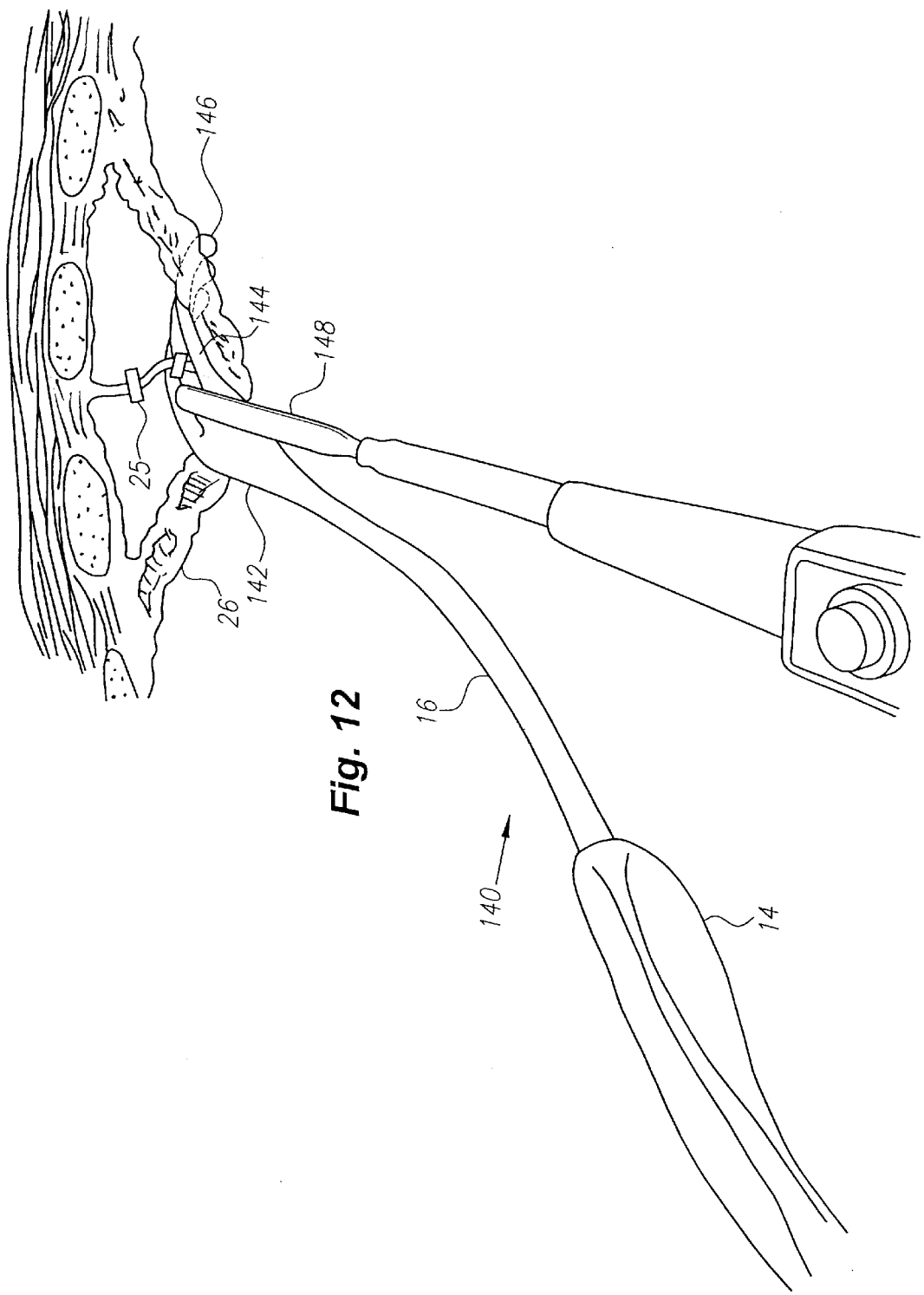
FIG. 12 is a perspective view showing a use of the invention including a fork configuration to assist in detaching the IMA.
Figure 13:
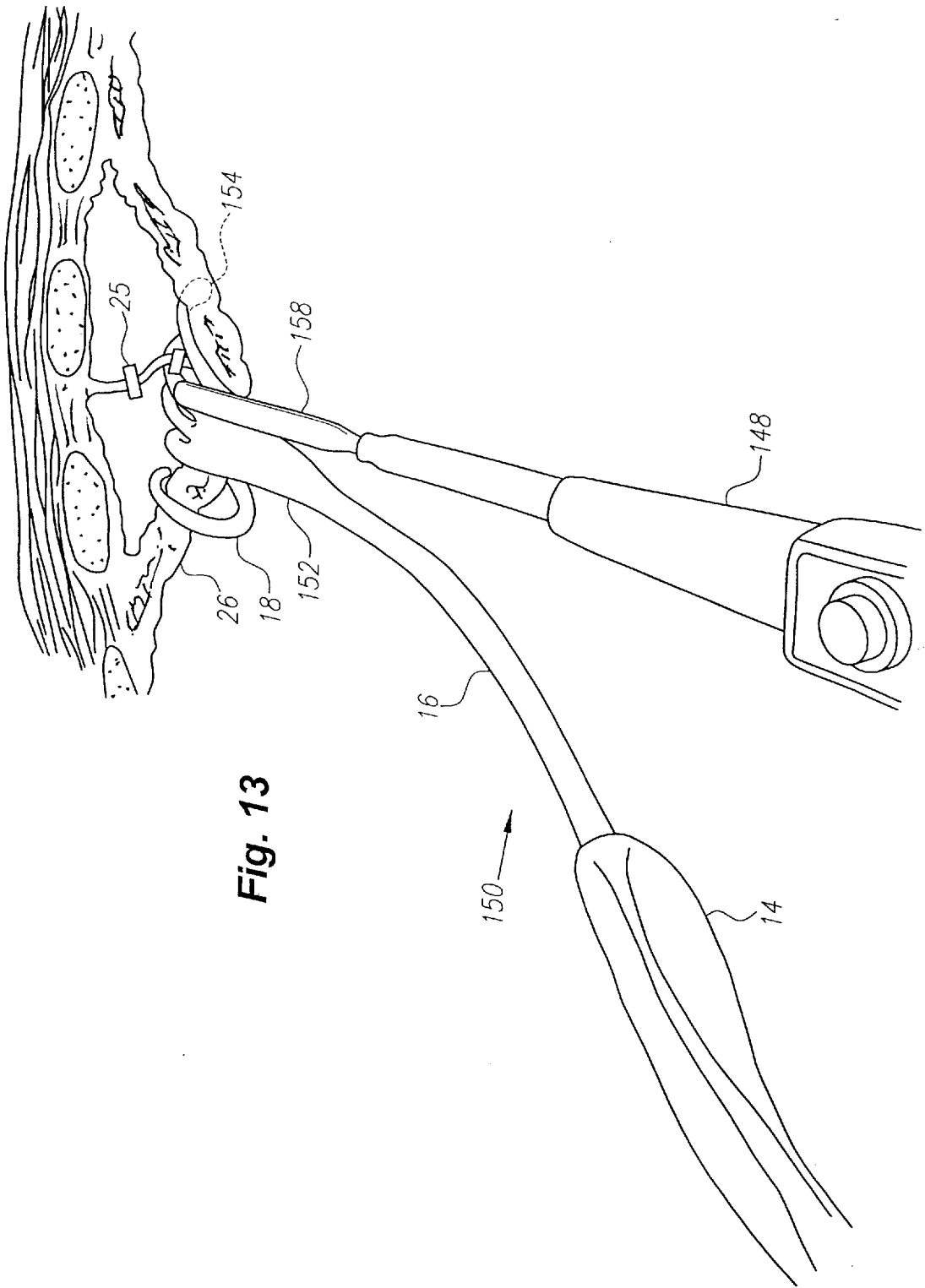
FIG. 13 is a perspective view illustrating the use of the invention including a fork configuration combined with a loop to assist in detaching the IMA.

An alternative preferred embodiment of the invention comprising a fork configuration at the distal working end of rod 16 is illustrated in FIGS. 10, 11A–11C, 12, 13, and 14. The fork configuration may be combined with loop 18 as depicted in FIGS. 10 and 13 or with arcuate configuration 30 or partial loop configuration 36 shown in FIGS. 4 and 5 respectively; alternatively a fork configuration may be used in place of loop 18 or equivalents at the distal working end of rod 16. It is to be understood that a fork configuration may be combined with malleable rod section 20, handle 14, retractable rod 50, hollow handle 42, actuating means 54, or any other element described herein.

Proceeding, FIG. 10 illustrates an embodiment 100 in which fork configuration 102 and loop 18 are combined at the distal working end of rod 16. Fork configuration 102 comprises a plurality of fingers 104 projecting from the distal end of the fork configuration. For purposes of illustration a finger 104 is formed into a arcuate or circular configuration, such as loop 18, terminating in tip 19. The diameter of the loop portion 18 of finger 104 may be slightly tapered from its proximal connection point to tip 19. Preferably, loop 18 is between about 270° and 360°. Tip 19 and the tips of fingers 104 preferably end in a bulbous configuration or have a tear drop shape. Fork 102 may comprise at least two and up to any greater number of fingers 104, one or more of which may be formed into a loop or equivalent, depending on the detailed design of embodiment 100. Likewise the lengths, widths, and spacings of fingers 104 may be chosen to be equal or unequal in any order at the discretion of the instrument designer. Fingers 104 may be straight, bent, curved, or adjustably shaped at the discretion of the designer.

FIGS. 11A–11C illustrate fork configurations at the distal working end of rods 16 having fingers of unequal lengths. FIG. 11A shows a fork 110 having inner finger 114 shorter than outer fingers 112 and 116. FIG. 11B shows a fork 120 in which left-hand outer finger 112 is shortest, inner finger 114 is intermediate in length, and right-hand outer finger 116 is longest. FIG. 11C shows a fork 130 having inner finger 114 longer than outer fingers 112 and 116. Preferably, any two adjacent fingers define a rounded "V"-shape groove to accommodate vessels of varying diameters for scraping or dissecting tissue away from a vessel.

FIG. 12 illustrates a manner of use of the invention employing an embodiment 140 comprising a fork configuration 142. In the illustrated embodiment a fork 142 is connected to the distal working end of rod 16, which is fastened to handle 14. Fork 142 comprises fingers 144, which terminate at their distal ends in enlarged hemispherical or rounded tips 146. Tips 146 are configured to make gentle atraumatic contact with a patient's tissue. In the illustrated procedure fork 142 gently captures, retracts, and stabilizes IMA segment 26 or other tubular organ away from its connective tissue. The IMA and/or separated and clipped side branch and tissue 25 may be captured and woven between fingers 144 to provide additional control and stability. Combination of a malleable rod 20 (FIG. 1) and adjustable finger shapes provide the surgeon with a wide range of angular motion through a small minimally invasive incision. An electrosurgical knife 148, such as a "Bovie" or such as that described in U.S. Pat. No. 5,013,312, may then be employed by the surgeon to coagulate and cut off side branch 25 from IMA 26. Fingers 144 provide a sliding guide surface for knife 148 to cut off side branch 25 cleanly and accurately, and protect IMA 26 from accidental injury by the knife. Instrument 140 positions, stabilizes, and protects IMA 26 during the described dissection procedure, reducing the time and risk of the procedure.

FIG. 13 illustrates a manner of use of the invention employing an embodiment 150 comprising a fork configuration 152 combined with loop 18 at the distal working end of rod 16 affixed to handle 14. In the illustrated procedure loop 18 captures and gently stabilizes IMA 26. Fingers 154 of fork 152 are curved to engage and retract IMA 26 and to separate side branch 25 between fingers 154. The surface defined by adjacent fingers 154 protects IMA 26 and provides a sliding support to guide electrosurgical knife 148 to coagulate and cut off side branch 25 quickly, accurately, and safely, reducing the time and risk of the procedure. Embodiment 150 illustrates the cooperative action between fork 152 and loop 18, wherein the loop controls IMA 26, while the fork captures side branch 25 and guides knife 148. This functionality potentially reduces the need for extra instruments in the small operating field.

Figure 14:
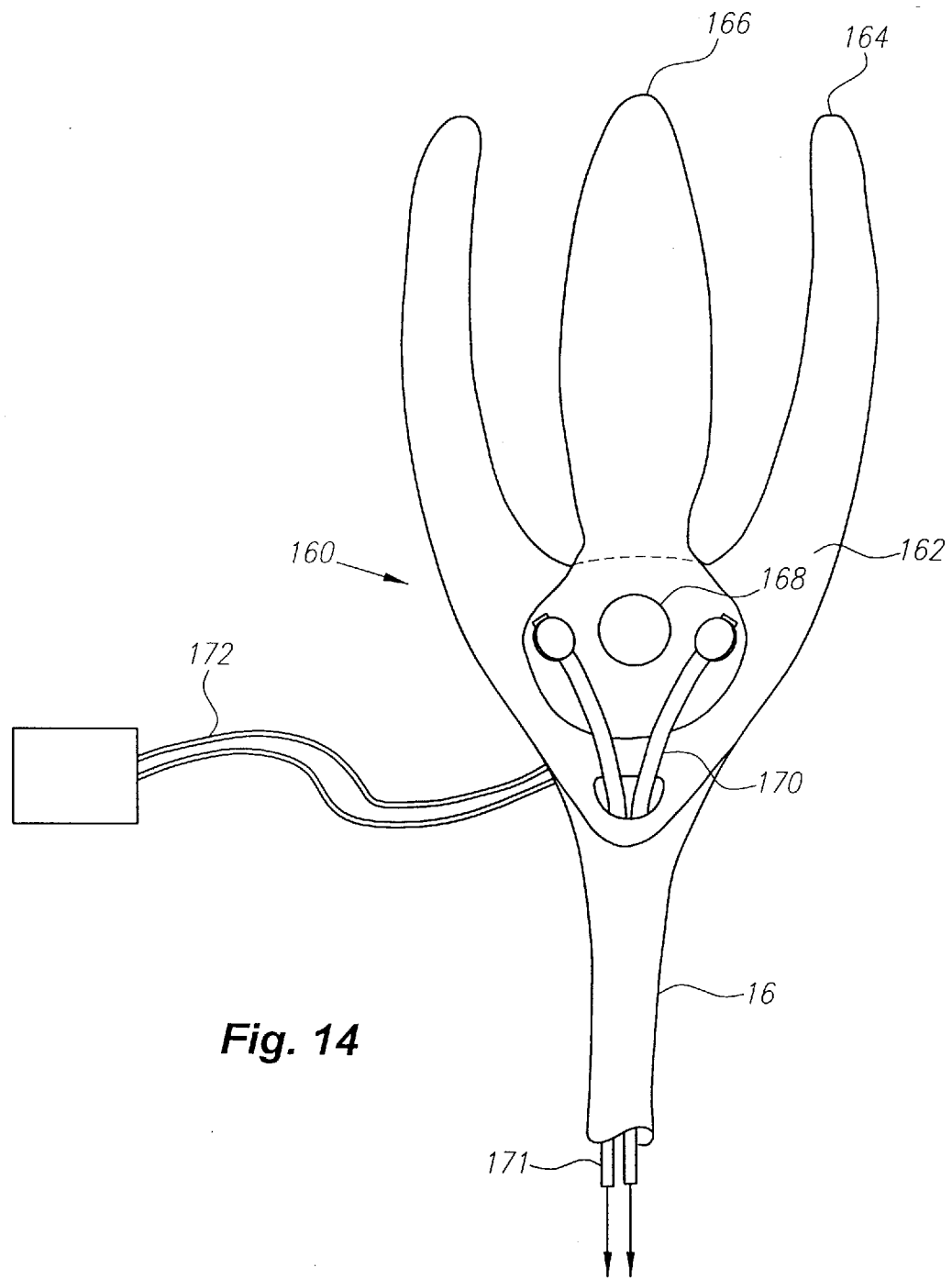
FIG. 14 shows an embodiment of the invention comprising a fork having an articulating finger and equipped with electrosurgical capability.

FIG. 14 depicts an embodiment 160 of the invention comprising a fork 162 having an articulating finger 166. In the illustration of FIG. 14 inner finger 166 is pivotally connected to fork 162 by means of pivot bearing 168 and toggles either right or left to engage an outer stationary finger 164. Alternatively outer fingers may pivot to engage an inner finger. For purposes of illustration only, articulating finger 166 may be actuated by cable mechanism 170. Pulling on the right-hand cable as illustrated by the arrows 171 pivots articulating finger 166 to the right, and pulling on the left-hand cable pivots articulating finger 166 to the left. Other actuating mechanisms, such as push rods, may alternatively be employed. Fingers 164 and 166 may include cutting blade edges, clamping jaws, or grasping surfaces. Embodiment 160 may comprise only mechanical elements, or may provide for unipolar or bipolar electrosurgery by means of electrical leads 172 connected to a suitable energy source. For example articulating finger 166 may be electrically insulated from stationary fingers 164 and connected to a unipolar electrical energy source by means of electrical leads 172, or articulating finger 166 may be electrically insulated from stationary fingers 164 with fingers 166 and 164 connected respectively to opposite poles of a bipolar electrical energy source by means of electrical leads 172. Those skilled in the art will recognize that alternative electrode arrangements may be used with the present invention.

Embodiment 160 can function as an electrosurgical fork 162 with all mechanically stationary fingers 164. One or more fingers 164 may be configured with cutting edges and connected to unipolar or bipolar energy sources. In this configuration the electrically active fingers may serve as electrosurgical cutting or coagulating ("Bovie") knives. In a configuration comprising one or more articulating fingers 166, embodiment 160 can function as electrosurgical scissors, wherein the knife edge of one finger engages another finger.

In operation embodiment 160 may be used to capture, engage, manipulate, clamp, coagulate, and cut vessels such as the IMA and side branches, tubular body organs, and related tissue. Use of embodiment 160 to coagulate and cut potentially eliminates the need for a separate electrosurgical knife, thereby reducing the number of instruments in the minimal operating field and thus increasing visibility and freedom of motion therein. When used alone or in combination with electrically insulated instruments embodiment 160 reduces the risk of accidental electrical shock or unwanted electrosurgical effects. Use of embodiment 160 further potentially reduces the need to apply mechanical surgical clips to side branches, thereby reducing the time for a procedure involving application and removal of mechanical clips, and reducing the risk of misplaced or lost mechanical surgical clips within the patient's body. A vessel or side branch can be woven and captured through the spaces between fingers 164 and 166, thereby exposing a greater length of vessel or side branch to coagulating energy, and insuring complete cauterization prior to cutting.

Although the invention has been described herein relative to specific embodiments, various additional features and advantages will be apparent from the description and drawings, and thus the scope of the invention is defined by the following claims and their equivalents.

What is claimed is:

1. A surgical apparatus for handling a graft vessel during a procedure of detaching the vessel from connecting tissues in its native location, comprising:
    an elongated slender rod of selected length; and
    a handle coaxially coupled to a proximal end of said rod;
    a distal end of said rod being terminated in a fork configuration having at least two finger shaped appendages for engaging the vessel and its connecting tissue and for protecting the vessel from injury during the detachment procedure wherein at least one of said finger configuration comprising a loop defining substantially a full circle and terminating in a tip located a sufficient distance from said loop to allow introducing the vessel past said loop to thereby engage the vessel within said loop.

2. The apparatus of claim 1 wherein a distal ends of said finger shaped appendages are terminated in enlarged rounded tips, whereby the vessel and its connecting tissue are engaged and manipulated in an atraumatic manner.

3. The apparatus of claim 1 wherein at least a partial length of a partial length of said rod is formed of a malleable material; whereby said rod may be bent to achieve a larger angular range of motion to facilitate capturing and handling the artery while it is being detached.

4. The apparatus of claim 1 wherein at least a partial length of said rod is coated with an electrically non-conductive material.

5. The apparatus of claim 1 wherein said finger shaped appendages are adjustably bendable into curved configurations, whereby the vessel and its connecting tissue are effectively captured and shielded from injury.

6. The apparatus of claim 1 further comprising:
    an elongated tube coaxially affixed to said handle and having a lumen therein for slidably housing said rod;
    said handle including a lumen therein for slidably receiving a selected proximal length of said rod; and
    actuating means integral with said handle for reciprocating said rod and said fork configuration into and from said tube.

7. The apparatus of claim 1 wherein at least one of said finger shaped appendages is pivotally attached to said fork configuration, whereby an actuating mechanism causes said pivotally attached appendage to toggle.

8. The apparatus of claim 1 wherein at least one of said finger shaped appendages is equipped with a cutting blade edge.

9. The apparatus of claim 8 further comprising:
    electrodes applied to the surface of said at least one of said finger shaped appendages; and
    a unipolar or bipolar energy source electrically connected to said electrodes.

10. The apparatus of claim 1 wherein said curved configuration comprises a circular loop extending between about 270° and about 360°.

11. An apparatus for handling a graft vessel during a procedure of detaching the vessel from connecting tissues in its native location, comprising:
    an elongated slender rod terminating at its distal end in a selectively curved configuration comprising a loop defining a full circle and terminating in a tip located a sufficient distance from the loop to allow introducing the vessel past the loop to thereby engage the vessel within the loop;
    a handle coaxially secured to the proximal end of said rod to facilitate the handling of said curved configuration, wherein said curved configuration is capable of capturing the vessel to facilitate handling the vessel while it is being detached; and
    wherein at least a partial length of said rod is formed of a malleable material.

* * * * *